US007632926B2

(12) United States Patent
Kim et al.

(10) Patent No.: US 7,632,926 B2
(45) Date of Patent: Dec. 15, 2009

(54) HUMANIZED MONOCLONAL ANTIBODIES TO HEPATOCYTE GROWTH FACTOR

(75) Inventors: Kyung Jin Kim, Cupertino, CA (US); Hangil Park, San Francisco, CA (US); Lihong Wang, Palo Alto, CA (US); Maximiliano Vasquez, Palo Alto, CA (US)

(73) Assignee: Galaxy Biotech, LLC, Cupertino, CA (US)

( * ) Notice: Subject to any disclaimer, the term of this patent is extended or adjusted under 35 U.S.C. 154(b) by 0 days.

(21) Appl. No.: 11/731,774

(22) Filed: Mar. 29, 2007

(65) Prior Publication Data

US 2008/0019974 A1 Jan. 24, 2008

Related U.S. Application Data

(60) Provisional application No. 60/788,243, filed on Apr. 1, 2006.

(51) Int. Cl.
| | |
|---|---|
| *C07K 16/00* | (2006.01) |
| *C07K 16/24* | (2006.01) |
| *C07K 16/26* | (2006.01) |
| *A61K 39/00* | (2006.01) |
| *A61K 39/395* | (2006.01) |

(52) U.S. Cl. .............................. 530/388.23; 530/387.1; 530/388.1; 530/388.15; 530/388.24; 424/130.1; 424/141.1; 424/142.1; 424/145.1

(58) Field of Classification Search ........................ None
See application file for complete search history.

(56) References Cited

U.S. PATENT DOCUMENTS

| | | | |
|---|---|---|---|
| 5,004,805 A | | 4/1991 | Gohda et al. |
| 5,530,101 A | * | 6/1996 | Queen et al. ............. 530/387.3 |
| 5,646,036 A | | 7/1997 | Schwall et al. |
| 5,686,292 A | | 11/1997 | Schwall et al. |
| 5,707,624 A | | 1/1998 | Nickoloff et al. |
| 5,859,205 A | | 1/1999 | Adair et al. |
| 5,997,868 A | | 12/1999 | Goldberg et al. |
| 6,099,841 A | | 8/2000 | Schwall et al. |
| 6,180,370 B1 | | 1/2001 | Queen et al. |
| 6,207,152 B1 | | 3/2001 | Schwall et al. |
| 6,214,344 B1 | | 4/2001 | Schwall et al. |
| 6,432,406 B1 | | 8/2002 | Goldberg et al. |
| 6,468,529 B1 | | 10/2002 | Schwall et al. |
| 6,639,055 B1 | | 10/2003 | Carter et al. |
| 7,220,410 B2 | * | 5/2007 | Kim et al. ................. 424/133.1 |
| 2004/0110685 A1 | | 6/2004 | Brandt et al. |
| 2004/0208876 A1 | | 10/2004 | Kim |
| 2005/0019327 A1 | * | 1/2005 | Kim et al. ................. 424/145.1 |
| 2007/0036797 A1 | | 2/2007 | Kim |
| 2007/0160613 A1 | | 7/2007 | Kim |

FOREIGN PATENT DOCUMENTS

| | | |
|---|---|---|
| CL | 01624-2002 | 7/2001 |
| WO | WO 01/34650 A1 | 5/2001 |
| WO | WO 03/057155 A2 | 7/2003 |
| WO | WO 2005/001486 A1 | 1/2005 |
| WO | WO 2005/007193 A2 | 1/2005 |
| WO | WO 2005/017107 A2 | 2/2005 |
| WO | WO 2005/044848 A1 | 5/2005 |
| WO | WO 2005/107800 A1 | 11/2005 |
| WO | WO 2006/130773 A2 | 12/2006 |

OTHER PUBLICATIONS

Rudikoff et al. PNAS 1982 79:1979-1983.*
Morrsion et al. Adv. Immunol. 1989, 44: 66-92.*
U.S. Appl. No. 60/788,243, filed Apr. 1, 2006, Kim.
U.S. Appl. No. 60/751,092, filed Dec. 15, 2005, Kim.
U.S. Appl. No. 60/687,118, filed Jun. 2, 2005, Kim.
U.S. Appl. No. 60/464,061, filed Apr. 18, 2008, Kim.
U.S. Appl. No. 11/818,305, filed Jun. 13, 2007, Kim et al.
U.S. Appl. No. 11/731,774, filed Mar. 29, 2007, Kim.
Abounader et al., "Reversion of Human Glioblastoma Malignancy by U1 Small Nuclear RNA/Ribozyme Targeting of Scatter Factor/Hepatocyte Growth Factor and c-met Expression," *J Natl Cancer Inst*, 91:1548-1556 (1999).
Advisory Action mailed Dec. 19, 2006 for U.S. Appl. No. 10/917,915.
Advisory Action mailed Oct. 30, 2006 for U.S. Appl. No. 10/917,915.
Anti-Human Hepatocyte Growth Factor (HGF) Developed in Goat, Affinity Isolated Antibody, product No. H7157, brochure for Sigma®.
Birchmeier et al., "Met, Metastasis, Motility and More," *Nature Reviews*, 4:915-925 (2003).
Brockmann et al., "Inhibition of Intracerebral Glioblastoma Growth by Local Treatment with the Scatter Factor/Hepatocyte Growth Factor-Antagonist NK4," *Clinical Cancer Research*, 9:4578-4585 (2003).
Burgess et al., "Fully Human Monoclonal Antibodies to Hepatocyte Growth Facto with Therapeutic Potential against Hepocyte Growth Factor/c-Met-Dependent human Tumors," *Cancer Res.*, 66(3):1721-1729 (2006).
Burr et al., "Anti-Hepatocyte Growth Factor Antibody Inhibits Hepatocyte Proliferation During Liver Regeneration," *Journal of Pathology*, 185:298-302 (1998).
Cao et al., "Neutralizing monoclonal antibodies to hepatocyte growth factor / scatter factor (HGF / SF) display antitumor activity in animal models," *PNAS*, 98(13):7443-7448 (2001).

(Continued)

*Primary Examiner*—Phillip Gambel
*Assistant Examiner*—Sharon Wen
(74) *Attorney, Agent, or Firm*—Townsend and Townsend and Crew LLP

(57) ABSTRACT

The present invention is directed toward a humanized neutralizing monoclonal antibody to hepatocyte growth factor, a pharmaceutical composition comprising same, and methods of treatment comprising administering such a pharmaceutical composition to a patient.

8 Claims, 8 Drawing Sheets

OTHER PUBLICATIONS

Danilkovitch-Miagkova et al., "Dysregulation of Met receptor tyrosine kinase activity in invasive tumors," *J. Clinical Investigation*, 109(7):863-867 (2002).

Date et al., "Inhibition of tumor growth and invasion by a four kringle antagonist (HGF / NK4) for hepatocyte growth factor," *Oncogene*, 17:3045-3054 (1998).

Davies et al., "The HGF/SF Antagonist NK4 Reversed Fibroblast- and HGF-Induced prostate Tumor Growth and Angiogenesis in Vivo," *Int. J. Cancer*, 106:348-354 (2003).

Di Nicola et al., "Human bone marrow stromal cells suppress T-lymphocyte proliferation induced by cellular or nonspecific mitogenic stimuli," *Blood*, 99(10):3838-3843 (2002).

Examiner Interview Summary mailed Oct. 26, 2006 for U.S. Appl. No. 10/917,915.

Hayashi et al., "Autocrine-Paracrine Effects of Overexpression of Heptocyte Growth Factor Gene on Growth of Endothelial Cells," *Biochem Biophys. Res. Comm.*, 220:539-545 (1996).

International Preliminary Report on Patentability with Written Opinion for PCT/US04/26565 mailed Jan. 7, 2005.

International Search Report for PCT/US04/26565 mailed Jan. 7, 2005.

Kermorgant et al., "Hepatocyte growth factor induces colonic cancer cell invasiveness via enhanced motility and protease overproduction. Evidence for PI3 kinase involvement," *Carcinogenesis*, 22(7):1035-1042 (2001).

Kim et al., "Systemic Anti-Hepatocyte Growth Factor Monoclonal Antibody Therapy Induces the Regression of Intracranial Glioma Xenografts," *Clin. Cancer Res.*, 12(4):1292-1298 (2006).

Koochekpour et al., "Met and Hepatocyte Growth Factor/Scatter Factor Expression in Human Gliomas(1)," *Cancer Research*, 57:5391-5398 (1997).

Kuba et al., "HGF/NK4, a Four-Kringle Antagonist of Hepatocyte Growth Factor, Is an Angiogenesis Inhibitor that Suppresses Tumor Growth and Metastasis in Mice," *Cancer Research*, 60:6737-6743 (2000).

Maulik et al., "Role of the hepatocyte growth factor receptor, c-Met, in oncogenesis and potential for therapeutic inhibition," *Cytokine & Growth Factor Reviews*, 13:41-59 (2002).

Michieli et al., "Targeting the tumor and its microenvironment by a dual-function decoy Met receptor," *Cancer Cell*, 6:61-73 (2004).

Nishimura et al., "Prostate Stromal Cell-Derived Hepatocyte Growth Factor Induces Invasion of Prostate Cancer Cell Line DUI 45 Through Tumor-Stromal Interaction," *Prostate*, 41:145-153 (1999).

Office Action mailed Jan. 10, 2006 for U.S. Appl. No. 10/917,915.

Office Action mailed Mar. 14, 2006 for U.S. Appl. No. 10/917,915.

Office Action mailed Aug. 11, 2006 for U.S. Appl. No. 10/917,915.

Prat et al., "Agonistic monoclonal antibodies against the Met receptor dissect the biological responses to HGF," *Journal of Cell Science*, 111:237-247 (1998).

Principal Investigator: Jin K. Kim, Abstract of Grant No. 2R44CA101283-02, "Novel Monoclonal Antibody Therapy for Cancer," pp. 1-2 from CRISP database, published *ca.* Aug. 2005.

Principal Investigator: Jin K. Kim, Abstract of Grant No. 1R43CA101283-01A1, "Novel Monoclonal Antibody Therapy for Cancer," pp. 1-2 from CRISP database, published *ca.* Apr. 2004.

Principal Investigator: John L. Lattera, Abstract of Grant No. 2R01NS032148-04, "Biochemistry of Brain Tumor Microvessel Development," pp. 1-2 printed from CRISP, published *ca.* (1998).

Response dated Jan. 18, 2007 to Final Office Action mailed Aug. 11, 2006 for U.S. Appl. No. 10/917,915.

Response dated Nov. 15, 2006 to Final Office Action mailed Aug. 11, 2006 for U.S. Appl. No. 10/917,915.

Response dated Apr. 14, 2006 to Office Action mailed Mar. 14, 2006 for U.S. Appl. No. 10/917,915.

Response dated Jan. 27, 2006 to Restriction Requirement mailed Jan. 10, 2006 for U.S. Appl. No. 10/917,915.

Response Draft for Discussion with Examiner Only submitted Oct. 16, 2006 to Final Office Action mailed Aug. 11, 2006 for U.S. Appl. No. 10/917,915.

Schwall et al., "Inhibition of cmet activation by a one-armed antibody," *Proceedings of AACR*, # 1424 from vol. 45 (2004).

Supplemental Amendment dated Apr. 25, 2006 for U.S. Appl. No. 10/917,915.

Supplementary Partial European Search Report for European Application No. 04781281 dated Mar. 6, 2007.

Zaccolo et al., "Dimerization of Fab fragments enables ready screening of phage antibodies that affect hepatocyte growth factor/scatter factor activity on target cells," *Eur. J. Immunol.*, 27:618-623 (1997).

Fan et al., "Comparison of the three-dimensional structures of a humanized and a chimeric Fab of an anti-gamma-interferon antibody", *J Mol Recognit* 12(1): 19-32 (1999).

Kashmiri et al., "SDR grafting—a new approach to antibody humanization", *Methods: A Companion to Methods in Enzymology* 36(1): 25-34 (2005).

Kim et al., "Antibody engineering for the development of therapeutic antibodies", *Molecules and Cells* 20(1): 17-29 (2005).

Pischla et al., "The crystal structure of a Fab fragment to the melanoma-associated GD2 ganglioside", *J Struct Biol* 119(1) 6-16 (1997).

Presta et al., "Humanization of an anti-vascular endothelial growth factor monoclonal antibody for the therapy of solid tumors and other disorders", *Cancer Res* 57(20) (1997).

Schwede et al., "Swiss-Model: An automated protein homology-modeling server", *Nucleic Acids Res.* 31(13): 3381-5 (2003).

Tsurushita et al., "Design of humanized antibodies: From anti-Tac to Zenapax" *Methods: A Companion to Methods in Enzymology* 36(1): 69-83 (2005).

Supplementary European Search Report for corresponding application EP 07759598.1, mailed Sep. 14, 2009.

Search report for corresponding Chilean Patent Application No. 886-2007, mailed Jul. 29, 2009.

* cited by examiner

A

```
                  1          2          3
     123456789  0123456789 0123456789 0123456789
     QVQLQQSGA  DLMKPGASVK ISCKATGYTF SGNWIEWVKQ 4           5 a        6          7
0123456789  01223456789 0123456789 0123456789
RPGHGLEWIG  EILPGSGNTNY NEKFKGKATF TADTSSNTAY 8 abc         9          10abc        11
0122223456789 0123456789 0000123456789 0123
MQLSSLTSEDSAV YYCARGGHYY GSSWDYWGQGTTL TVSS
```

B

```
                  1          2          3
     123456789  0123456789 0123456789 0123456789
     NIVMTQSPK  SMSMSVGERV TLTCKASENV VTYVSWYQQK 4           5          6          7
0123456789  0123456789 0123456789 0123456789
PEQSPKLLIY  GASNRYTGVP DRFTGSGSAT DFTLTISSVQ 8           9          10
0123456789  0123456789 012345678
AEDLADYHCG  QGYSYPYTFG GGTKLEIKR
```

```
                          1           2           3
              123456789   0123456789  0123456789  0123456789
L2G7          QVQLQQSGA   DLMKPGASVK  ISCKATGYTF  SGNWIEWVKQ
HuL2G7        EVQLVQSGA   EVKKPGASVK  VSCKVSGYTF  SGNWIEWVRQ
AAC18323      QVQLVQSGA   EVKKPGASVK  VSCKVSGYTL  TelsmhWVRQ 4           5    a      6           7
              0123456789  01223456789 0123456789  0123456789
L2G7          RPGHGLEWIG  EILPGSGNTNY NEKFKGKATF  TADTSSNTAY
HuL2G7        APGKGLEWIG  EILPGSGNTNY NEKFKGKATM  TADTSTDTAY
AAC18323      APGKGLEWMG  gfdpedgetiy aqkfqgRVTM  TEDTSTDTAY 8    abc       9          10abc         11
              0122223456789 0123456789  0000123456789 0123
L2G7          MQLSSLTSEDSAV YYCARGGHYY  GSSWDYWGQGTTL TVSS
HuL2G7        MELSSLRSEDTAV YYCARGGHYY  GSSWDYWGQGTLV TVSS
AAC18323      MELSSLRSEDTAV YYCATpvgrc  sst*dyWGQGTLV TVSS
```

* insertion of scyhpl between sst and dyW

B

```
                          1           2           3
              123456789   0123456789  0123456789  0123456789
L2G7          NIVMTQSPK   SMSMSVGERV  TLTCKASENV  VTYVSWYQQK
HuL2G7        DIVMTQSPS   SLSASVGDRV  TITCKASENV  VTYVSWYQQK
BAC01726      DIQMTQSPS   SLSASVGDRV  TITCrasqsi  ssylnWYQQK 4           5           6           7
              0123456789  0123456789  0123456789  0123456789
L2G7          PEQSPKLLIY  GASNRYTGVP  DRFTGSGSAT  DFTLTISSVQ
HuL2G7        PGKAPKLLIY  GASNRYTGVP  DRFSGSGSGT  DFTLTISSLQ
BAC01726      PGKAPKLLIY  AasslqsGVP  SRFSGSGSGT  DFTLTISSLQ 8           9           10
              0123456789  0123456789  012345678
L2G7          AEDLADYHCG  QGYSYPYTFG  GGTKLEIKR
HuL2G7        PEDFATYYCG  QGYSYPYTFG  QGTKLEIKR
BAC01726      PEDFATYYCq  qsystpytFG  QGTKLEIKR
```

HUMANIZED MONOCLONAL ANTIBODIES TO HEPATOCYTE GROWTH FACTOR

CROSS-REFERENCE TO RELATED APPLICATION

The present application is a nonprovisional of U.S. Ser. No. 60/788,243 filed Apr. 1, 2006, which is incorporated by reference in its entirety for all purposes.

STATEMENT OF GOVERNMENT INTEREST

The work described in this application was funded in part by Grant 2R44CA101283-02 from the National Institutes of Health. The US government may have certain rights in this invention.

FIELD OF THE INVENTION

The present invention relates generally to the combination of monoclonal antibody (mAb) and recombinant DNA technologies for developing novel biologics, and more particularly, for example, to the production of humanized monoclonal antibodies that bind to and neutralize Hepatocyte Growth Factor.

BACKGROUND OF THE INVENTION

Human Hepatocyte Growth Factor (HGF) is a multifunctional heterodimeric polypeptide produced by mesenchymal cells. HGF has been shown to stimulate angiogenesis, morphogenesis and motogenesis, as well as the growth and scattering of various cell types (Bussolino et al., J. Cell. Biol. 119: 629, 1992; Zarnegar and Michalopoulos, J. Cell. Biol. 129: 1177, 1995; Matsumoto et al., Ciba. Found. Symp. 212:198, 1997; Birchmeier and Gherardi, Trends Cell. Biol. 8:404, 1998; Xin et al. Am. J. Pathol. 158:1111, 2001). The pleiotropic activities of HGF are mediated through its receptor, a transmembrane tyrosine kinase encoded by the proto-oncogene cMet. In addition to regulating a variety of normal cellular functions, HGF and its receptor c-Met have been shown to be involved in the initiation, invasion and metastasis of tumors (Jeffers et al., J. Mol. Med. 74:505, 1996; Comoglio and Trusolino, J. Clin. Invest. 109:857, 2002). HGF/cMet are coexpressed, often over-expressed, on various human solid tumors including tumors derived from lung, colon, rectum, stomach, kidney, ovary, skin, multiple myeloma and thyroid tissue (Prat et al., Int. J. Cancer 49:323, 1991; Chan et al., Oncogene 2:593, 1988; Weidner et al., Am. J. Respir. Cell. Mol. Biol. 8:229, 1993; Derksen et al., Blood 99:1405, 2002). HGF acts as an autocrine (Rong et al., Proc. Natl. Acad. Sci. USA 91:4731, 1994; Koochekpour et al., Cancer Res. 57:5391, 1997) and paracrine growth factor (Weidner et al., Am. J. Respir. Cell. Mol. Biol. 8:229, 1993) and anti-apoptotic regulator (Gao et al., J. Biol. Chem. 276:47257, 2001) for these tumors.

HGF is a 102 kDa protein with sequence and structural similarity to plasminogen and other enzymes of blood coagulation (Nakamura et al., Nature 342:440, 1989; Weidner et al., Am. J. Respir. Cell. Mol. Biol. 8:229, 1993). Human HGF is synthesized as a 728 amino acid precursor (preproHGF), which undergoes intracellular cleavage to an inactive, single chain form (proHGF) (Nakamura et al., Nature 342:440, 1989; Rosen et al., J. Cell. Biol. 127:1783, 1994). Upon extracellular secretion, proHGF is cleaved to yield the biologically active disulfide-linked heterodimeric molecule composed of an a-subunit and β-subunit (Nakamura et al., Nature 342:440, 1989; Naldini et al., EMBO J. 11:4825, 1992). The α-subunit contains 440 residues (69 kDa with glycosylation), consisting of the N-terminal hairpin domain and four kringle domains. The p-subunit contains 234 residues (34 kDa) and has a serine protease-like domain, which lacks proteolytic activity. HGF has two unique cell specific binding sites: a high affinity ($Kd=2\times10^{-10}$ M) binding site for the cMet receptor and a low affinity ($Kd=10^{-9}$ M) binding site for heparin sulfate proteoglycans (HSPG), which are present on the cell surface and extracellular matrix (Naldini et al., Oncogene 6:501, 1991; Bardelli et al., J. Biotechnol. 37:109, 1994; Sakata etal., J. Biol. Chem., 272:9457,1997).

The cMet receptor is a member of the class IV protein tyrosine kinase receptor family. The full length cMet gene was cloned and identified as the cMet proto-oncogene (Cooper et al., Nature 311:29, 1984; Park et al., Proc. Natl. Acad. Sci. USA 84:6379,1987). NK2 (a protein encompassing the N-terminus and first two kringle domains of the α-subunit) is sufficient for binding to cMet and activation of the signal cascade for motility, however the full length protein is required for the mitogenic response (Weidner et al., Am. J. Respir. Cell. Mol. Biol. 8:229, 1993). HSPG binds to HGF by interacting with the N terminus of HGF.

HGF/cMet have been reported to play important roles in several aspects of cancer development such as tumor initiation, invasion, metastasis, regulation of apoptosis and angiogenesis. Several different approaches have been investigated to obtain an effective antagonistic molecule: truncated HGF proteins such as NK1 (N terminal domain plus kringle domain 1; Lokker et al., J. Biol. Chem. 268:17145, 1993), NK2 (N terminal domain plus kringle domains 1 and 2; Chan et al., Science 254:1382,1991) and NK4 (N-terminal domain plus four kringle domains; Kuba et al., Cancer Res. 60:6737, 2000), anti-cMet mAbs (Dodge, Master's Thesis, San Francisco State University, 1998) and anti-HGF mAbs (Cao et al., Proc. Natl. Acad. Sci. USA 98:7443, 2001, which is incorporated herein by reference).

NK1 and NK2 can compete effectively with the binding of HGF to its receptor, but have been reported to have partial agonistic activities in vitro (Cioce et al., J. Biol. Chem. 271: 13110, 1996; Schwall et al., J. Cell Biol. 133:709, 1996), rather than purely antagonist activities as desired. More recently, Kuba et al., Cancer Res. 60:6737, 2000, reported that NK4 could partially inhibit the primary growth and metastasis of murine lung tumor LLC in a nude mouse model by continuous infusion of NK4. However, the fact that NK4 had to be administered continuously to obtain a partial growth inhibition of primary tumors indicates a potentially short half-life of the NK4 molecule and/or lack of potency.

Cao et al., Proc. Natl. Acad. Sci. USA 98:7443, 2001, reported that the administration of a cocktail of three anti-HGF mAbs, which were selected based upon their ability to inhibit the scattering activity of HGF in vitro, were able to inhibit the growth of human tumors in the xenograft nude mouse model. They postulated that three mAbs recognizing three different binding sites on HGF were required to inhibit the bioactivities of HGF in vivo: two mAbs inhibited the binding of HGF to cMet and one mAb inhibited the binding of HGF to heparin.

Recently, human mAbs that individually bind and neutralize HGF developed using transgenic mouse technology have been reported (Burgess et al., WO 2005/017107A2 and Burgess et al., Cancer Res 66:1721, 2006, each of which is herein incorporated by reference for all purposes). However, of these at least the 2.12.1 mAb, which was apparently the most potent in tumor xenograft models, nonetheless did not inhibit angiogenesis. A mouse mAb L2G7 has been developed that neutralizes all tested biological activities of HGF including angiogenesis (Patent application U.S. Ser. No. 10/917,915 filed Aug. 13, 2004, and Kim et al. Clin Cancer Res 12:1292, 2006, each of which is herein incorporated by reference for all purposes).

Thus, there is a need for a humanized monoclonal antibody that blocks biological activity of HGF in vitro and in vivo. The present invention fulfills this and other needs.

SUMMARY OF THE CLAIMED INVENTION

In one embodiment, the invention provides a humanized neutralizing mAb to human Hepatocyte Growth Factor (HGF). The mAb inhibits at least one, and preferably several or all biological activities of HGF including binding to its receptor cMet, induction of scattering of cells such as Madin-Darby canine kidney cells, induction of proliferation of Mv 1 Lu mink lunk epithelial cells and/or hepatocytes and/or HUVEC, and stimulation of angiogenesis. A preferred humanized anti-HGF mAb inhibits, most preferably completely inhibits, growth of a human tumor xenograft in a mouse. In a preferred embodiment, the humanized mAb is a humanized L2G7 mAb. In an especially preferred embodiment, the heavy and light chain variable regions of the mAb have the sequences shown on the lines labeled HuL2G7 in FIG. 2A and FIG. 2B respectively, or sequences that are at least 90% or more identical to them. In another embodiment, the invention provides a humanized monoclonal antibody (mAb) that binds and neutralizes human Hepatocyte Growth Factor (HGF), the humanized antibody comprising humanized heavy and light chains. The humanized heavy chain comprises CDRs from L2G7 and a human heavy chain variable region framework provided that at least one position of the human heavy chain variable region framework selected from the group consisting of H29, H30, H48, H66, H67, H71, H94 is occupied by the amino acid occupying the corresponding position in the L2G7 heavy chain. The humanized light chain comprises CDRs from L2G7 and a human light chain variable region framework provided that at least one position selected from the group consisting of L3 and L60 is occupied by the amino acid occupying the corresponding position in the L2G7 light chain.

Cell lines producing such humanized antibodies are also provided. In another embodiment, a pharmaceutical composition comprising a humanized L2G7 mAb is provided. In a third embodiment, the pharmaceutical composition is administered to a patient (typically a human patient) to treat cancer or other disease.

BRIEF DESCRIPTION OF THE DRAWINGS

FIG. 1. Amino acid sequences of the L2G7 mature heavy chain (A) (SEQ ID NO: 2) and light chain (B) (SEQ ID NO: 3) variable regions translated from the cloned cDNAs. The CDRs are underlined. The Kabat numbering system is used.

FIG. 2. Amino acid sequences of the HuL2G7 heavy chain (A) (SEQ ID NO:5) and light chain (B) (SEQ ID NO: 8) mature variable regions are shown aligned with L2G7 (SEQ ID NOS:4 and 7) and acceptor V regions (SEQ ID NOS:6 and 9). The CDRs are underlined in the L2G7 sequences, and the amino acids substituted with mouse L2G7 amino acids are underlined in the HuL2G7 sequences, with the initial amino acid H1E double-underlined. The Kabat numbering system is used.

FIG. 3. Amino acid sequences of the entire HuL2G7 heavy chain (A) (SEQ ID NO: 10) and light chain (B) (SEQ ID NO:11). The first amino acids of the mature heavy and light chains (i.e., after cleavage of the signal sequences) are double underlined and labeled with the number 1; these amino acids are also the first amino acids of the mature V regions. In the heavy chain, the first amino acids of the CH1, hinge, CH2 and CH3 regions are underlined, and in the light chain, the first amino acid of the $C_K$ region is underlined.

DETAILED DESCRIPTION OF THE PREFERRED EMBODIMENTS

Figure 4:
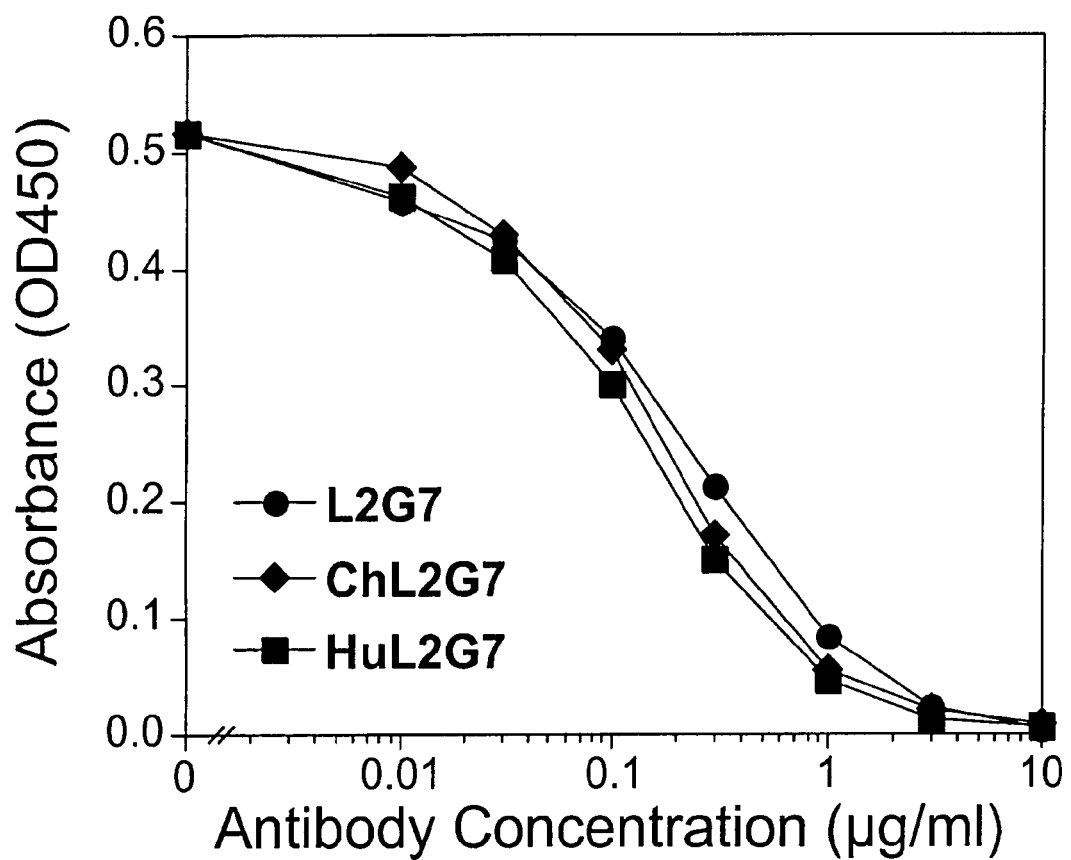
FIG. 4. Competitive binding assay of HuL2G7, ChL2G7 and L2G7 for binding to HGF.

The invention provides humanized neutralizing anti-HGF monoclonal antibodies, pharmaceutical compositions comprising them, and methods of using them for the treatment of disease.

1. Antibodies

Antibodies are very large, complex molecules (molecular weight of ~150,000 or about 1320 amino acids) with intricate internal structure. A natural antibody molecule contains two identical pairs of polypeptide chains, each pair having one light chain and one heavy chain; hence the fundamental structural unit of an antibody is a tetramer. Each light chain and heavy chain in turn consists of two regions: a variable ("V") region involved in binding the target antigen, and a constant ("C") region that interacts with other components of the immune system. The light and heavy chain variable regions fold up together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-D space to form the actual antibody binding site which locks onto the target antigen. The position and length of the CDRs have been precisely defined. See Kabat, E. et al., Sequences of Proteins of Immunological Interest, U.S. Department of Health and Human Services, 1983, 1987, which are herein incorporated by reference. The part of a variable region not contained in the CDRs is called the framework, which forms the environment for the CDRs. In each chain, the three CDRs are interspersed with four framework sections in this order: FR1, CDR1, FR2, CDR2, FR3, CDR3, FR4.

Amino acids from the variable regions of the mature heavy and light chains of immunoglobulins are designated Hx and Lx respectively, where x is a number designating the position of an amino acid according to the scheme of Kabat, op. cit. Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Moreover, any two antibody sequences can be uniquely aligned, for example to determine percent identity, by using the Kabat numbering system so that each amino acid in one antibody sequence is aligned with the amino acid in the other sequence that has the same Kabat number. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

A monoclonal antibody (mAb) is a single molecular species of antibody and therefore does not encompass polyclonal antibodies produced by injecting an animal (such as a rodent, rabbit or goat) with an antigen, and extracting serum from the animal. A humanized antibody is a genetically engineered (monoclonal) antibody in which the CDRs from a mouse antibody ("donor antibody", which can also be rat, hamster or other similar species) are grafted onto a human antibody ("acceptor antibody"). Humanized antibodies can also be made with less than the complete CDRs from a mouse antibody (e.g., Pascalis et al., J. Immunol. 169:3076, 2002). Most commonly the first heavy chain hypervariable loop H1 as defined by Chothia & Lesk, J. Mol. Biol. 196:901-917, 1987, from the donor antibody is also transferred to the humanized antibody. Thus, a humanized antibody is an antibody having CDRs from a donor antibody and variable region frameworks and constant regions from human antibodies. The light and heavy chain acceptor frameworks may be from the same or different human antibodies and may each be a composite of two or more human antibody frameworks; or alternatively may be a consensus sequence of a set of human frameworks (e.g., a subgroup of human antibodies as defined in Kabat et al, op. cit.), i.e., a sequence having the most commonly occurring amino acid in the set at each position. In addition, to retain high binding affinity, at least one of two additional structural elements can be employed. See, Queen et al., U.S. Pat. Nos. 5,530,101 and 5,585,089, each of which is incorporated herein by reference, which provide detailed instructions for construction of humanized antibodies.

In the first structural element, the framework of the heavy chain variable region of the humanized antibody is chosen to have high sequence identity (at least 65%) with the framework of the heavy chain variable region of the donor antibody, by suitably selecting the acceptor antibody from among the many known human antibodies. In the second structural element, in constructing the humanized antibody, selected amino acids in the framework of the human acceptor antibody (outside the CDRs) are replaced with corresponding amino acids from the donor antibody, in accordance with specified rules. Specifically, the amino acids to be replaced in the framework are generally chosen on the basis of their ability to interact with the CDRs. For example, the replaced amino acids can be adjacent to a CDR in the donor antibody sequence or within 4-6 angstroms of a CDR in the humanized antibody as measured in 3-dimensional space.

On the other hand, since humanized mAbs must originate with a non-human donor mAb, humanized mAbs do not encompass essentially human mAbs made by isolating nucleic acids encoding variable regions from a human and selecting them using phage display methods (see, e.g., Dower et al., WO91/17271; McCafferty et al., WO92/001047; Winter, WO92/20791; and Winter, FEBS Lett. 23:92, 1998) or by using transgenic mice (see, e.g., Lonberg et al., WO93/12227; Kucherlapati WO91/10741, and Burgess et al. WO 2005/027107A2).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20 33 or 100× excess of one antibody inhibits binding of the other by at least 50% but preferably 75%, 90% or even 99% as measured in a competitive binding assay (see, e.g., Junghans et al., Cancer Res. 50:1495, 1990). Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

2. Humanized Neutralizing Anti-HGF Antibodies

A monoclonal antibody (mAb) that binds HGF (i.e., an anti-HGF mAb) is said to neutralize HGF, or be neutralizing, if the binding partially or completely inhibits one or more biological activities of HGF (i.e., when the mAb is used as a single agent). Among the biological properties of HGF that a neutralizing antibody may inhibit are the ability of HGF to bind to its cMet receptor, to cause the scattering of certain cell lines such as Madin-Darby canine kidney (MDCK) cells; to stimulate proliferation of (i.e., be mitogenic for) certain cells including hepatocytes, Mv 1 Lu mink lung epithelial cells, and various human tumor cells; or to stimulate angiogenesis, for example as measured by stimulation of human umbilical vascular endothelial cell (HUVEC) proliferation or tube formation or by induction of blood vessels when applied to the chick embryo chorioallantoic membrane (CAM). Antibodies of the invention preferably bind to human HGF, i.e., to the protein encoded by the GenBank sequence with Accession number D90334.

A humanized neutralizing mAb of the invention at a concentration of, e.g., 0.01, 0.1, 0.5, 1, 2, 5, 10, 20 or 50 μ/ml will inhibit a biological function of HGF (e.g., stimulation of proliferation or scattering) by about at least 50% but preferably 75%, more preferably by 90% or 95% or even 99%, and most preferably approximately 100% (essentially completely) as assayed by methods described under Examples or known in the art. Typically, the extent of inhibition is measured when the amount of HGF used is just sufficient to fully stimulate the biological activity, or is 0.01, 0.02, 0.05, 0.1, 0.5, 1, 3 or 10 μg/ml. Preferably, at least 25%, 50%, 75%, 90%, or 95% or essentially complete inhibition will be achieved when the molar ratio of antibody to HGF is 0.1×, 0.5×, 1×, 2×, 3×, 5× or 10×. Most preferably, the mAb will neutralize not just one but several of the biological activities listed above; for purposes herein, an anti-HGF mAb that neutralizes all the biological activities of HGF will be called "fully neutralizing", and such mAbs are most preferable.

MAbs of the invention preferably bind specifically to HGF, that is they will not bind, or only bind to a much lesser extent, proteins that are related to HGF such as fibroblast growth factor (FGF) and vascular endothelial growth factor (VEGF). MAbs of the invention typically have a binding affinity ($K_a$) for HGF of at least $10^7$ M$^{-1}$ but preferably $10^8$ M$^{-1}$ or higher, and most preferably $10^9$ M$^{-1}$ or higher or even $10^{10}$ M$^{-1}$ or higher.

Humanized mAbs of the invention include anti-HGF antibodies in their natural tetrameric form (2 light chains and 2 heavy chains) and can be of any of the known isotypes IgG, IgA, IgM, IgD and IgE and their subtypes, i.e., IgG1, IgG2, IgG3, IgG4 and may comprise a kappa or lambda light chain. The mAbs of the invention also include fragments of antibodies such as Fv, Fab and F(ab')$_2$; bifunctional hybrid antibodies (e.g., Lanzavecchia et al., Eur. J. Immunol. 17:105, 1987), single-chain antibodies (Huston et al., Proc. Natl. Acad. Sci. USA 85:5879, 1988; Bird et al., Science 242:423, 1988); and antibodies with altered constant regions (e.g., U.S. Pat. No. 5,624,821). The source of the CDRs of the mAb may be of animal (e.g., mouse, rat, hamster or chicken) origin, or they may be genetically engineered. Rodent mAbs are made by standard methods well-known in the art, comprising multiple immunization with HGF in appropriate adjuvant i.p., i.v., or into the footpad, followed by extraction of spleen or lymph node cells and fusion with a suitable immortalized cell line, and then selection for hybridomas that produce antibody binding to HGF.

The invention provides humanized forms of the mouse L2G7 mAb. The sequences of the mature heavy and light chain variable regions of the mouse L2G7 mAb are shown in FIGS. 1A and 1B respectively. Hence, humanized forms of the L2G7 mAb encompass most or all of the CDR amino acids from these sequences in human variable region frameworks (including single, composite or consensus sequence human frameworks). For example, some humanized antibodies include three intact CDRs from the L2G7 heavy chain and three intact CDRs from the light chain. Other humanized antibodies include at least one intact CDR from the L2G7 heavy chain and at least one intact CDR from the L2G7 light chain. Some humanized antibodies include at least one CDR in which some residues are from the corresponding CDR of L2G7 and the others are from a CDR of a human antibody, preferably the same human antibody as supplies the variable region framework containing the CDR.

In some humanized antibodies of the invention at least 1, 3, 5 or all positions selected from the group H29, H30, H48, H66, H67, H71, H94, L3, and L60 are occupied by an amino acid present at the corresponding position by Kabat numbering in the mouse L2G7 antibody. In the human acceptor variable region frameworks used in the Examples, all of these positions are occupied by human residues differing from the amino acid present at the corresponding position in the mouse L2G7 antibody. Thus, it is preferable to substitute all or most positions selected from the group. If other human variable region frameworks are used, some of the positions may be occupied by amino acids that are the same in the human variable region framework and the mouse L2G7 antibody. Accordingly, substitution is not performed at such positions but can be performed at other positions differing between the human variable region framework and mouse L2G7 antibody in accordance with the rules of Queen, U.S. Pat. No. 5,530,101 and U.S. Pat. No. 5,585,089. Regardless of the choice of human variable region framework, substitution of other amino acids besides those specified in the above group is also possible as discussed below. However, in general neither the heavy chain variable region framework nor the light chain variable region framework of the humanized antibody includes more than ten or twelve substitutions resulting in residues not present in the acceptor human variable region framework (including human consensus variable region frameworks and composite human variable region frameworks, as discussed above.)

Any constant regions present in the humanized antibodies of the invention are human or essentially so, having no more than ten, and preferably two or fewer substitutions relative to a natural human constant region. Some substitutions are advantageous in increasing the half-life of an antibody and/or its affinity for FcγRn, as discussed below. Other substitutions, usually conservative substitutions, as discussed below, are neutral in effect.

Exemplified humanized forms of L2G7 include mature heavy and light chain variable regions having the sequences shown in FIGS. 2A and 2B respectively. Other preferred forms of humanized L2G7 include mature heavy and light chain variable regions having sequences at least 90%, 95%, 98% or 99% identical to these sequences (when aligned according to Kabat numbering, supra), and/or differ from them by a small number (typically involving no more than 5 or 10 amino acids) of functionally inconsequential substitutions, deletions and/or insertions. For example, the first amino acid of the heavy chain may be either Glu or Gln. The substitutions are usually conservative, that is replace an amino acid with one that is chemically similar. For purposes of classifying amino acids substitutions as conservative or non-conservative, amino acids may be grouped as follows: Group I (hydrophobic sidechains): Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions are those that involve substitutions between amino acids in the same group. Substitutions relative to the V regions in FIGS. 2A and 2B are preferably avoided at positions H29, H30, H48, H66, H67, H71, H94, L3, and L60, where amino acids from mouse L2G7 were included due to the interaction of these positions with CDRs, as discussed in the Examples. Substitutions preferably occur in variable region framework positions, but can also occur in CDR regions. If a CDR region is substituted, it is preferable to replace a mouse amino acid with an amino acid from the corresponding position (Kabat numbering) of a human antibody, preferably the same human antibody that supplies the acceptor variable region frameworks.

Figure 3:
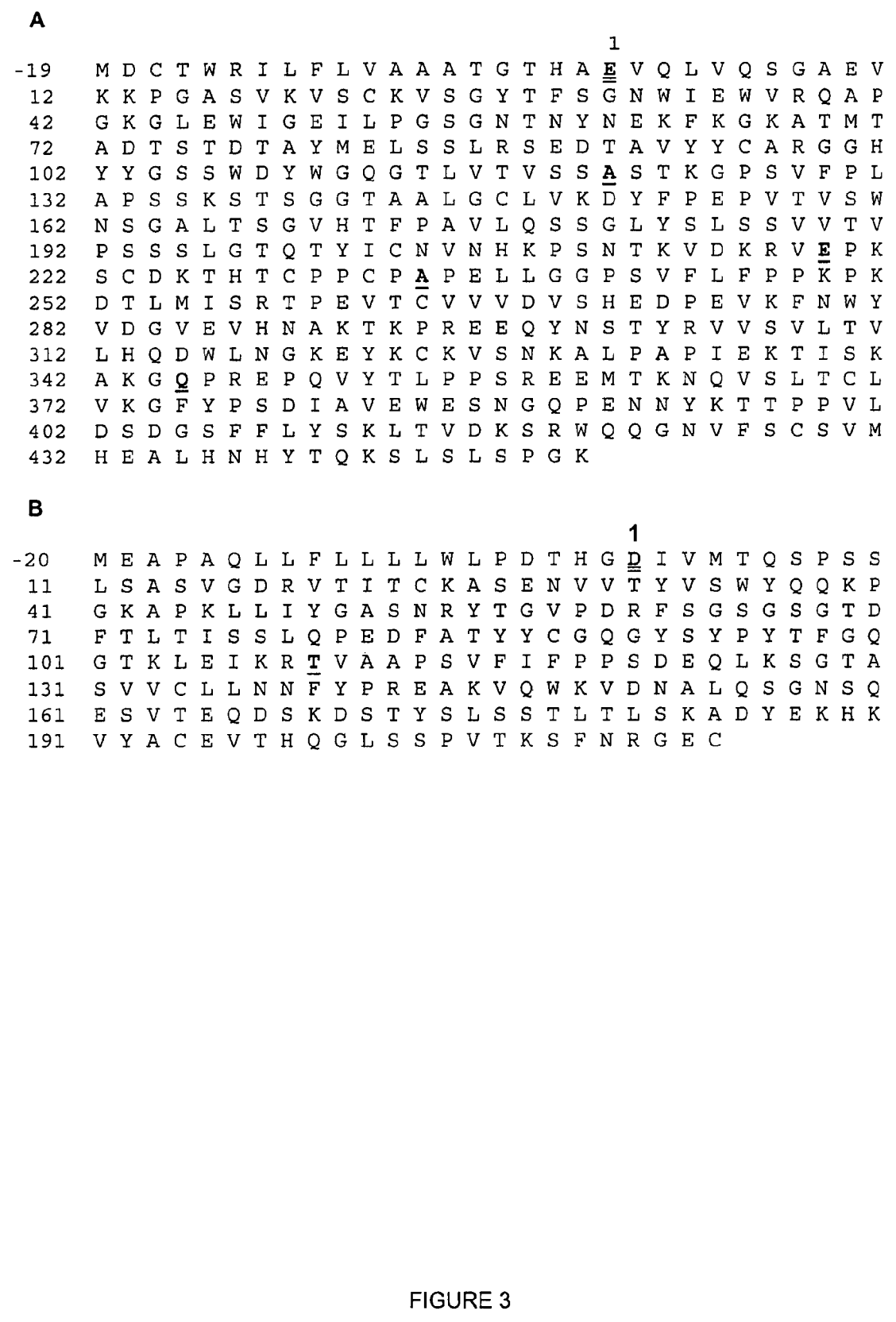

Usually, the humanized L2G7 mAbs are of the IgG1, IgG2, IgG3 or IgG4 isotype with a kappa light chain. An IgG1 mAb having the variable regions of FIGS. 2A and 2B respectively combined with complete human gamma-1 and kappa constant region is designated HuL2G7. The complete heavy and light chains of HuL2G7 are respectively shown in FIGS. 3A and 3B. Only the mature parts of these sequences beginning at the positions indicated by the number 1 actually constitute HuL2G7, as the preceding signal peptides are cleaved off before or during antibody secretion.

Variants of HuL2G7 retaining similar binding characteristics to HuL2G7 can be obtained by mutagenesis followed by mass selection using the phage display methods discussed above. Variants are initially selected for specific binding to HGF, optionally in competition with HuL2G7 or mouse L2G7. Variants having the same or similar binding characteristics as the exemplified antibody can then be tested functionally.

Preferred humanized L2G7 mAbs are neutralizing or fully neutralizing against HGF as defined supra. Preferably, for some, most or all biological properties of HGF measured (e.g., binding to Met, stimulation of proliferation of Mv 1 Lu or HUVEC cells), the neutralizing activity of the humanized mAb is within 3-fold, more preferably within 2-fold or 1.5-fold, and most preferably indistinguishable from (i.e., to within experimental error), the neutralizing activity of L2G7 itself. That is, no more than 3-fold, 2-fold, 1.5-fold or the same amount of humanized mAb relative to L2G7 is needed to obtain the same extent of inhibition of the biological property (for example, as measured by IC50's). Preferably, the affinity for HGF of the humanized mAbs is also within 3-fold, 2-fold or essentially indistinguishable from that of L2G7. Similarly, in xenograft mouse models (e.g., using a human glioma cell line such as U87), the humanized mAbs preferably inhibit tumor growth within 3-fold, 2-fold or indistinguishably from the mouse L2G7 mAb. Indeed, preferably only a 40, 20 or even 10 µg dose of humanized mAb administered twice per week completely inhibits growth of U87 tumor xenografts.

Humanized mAbs can be expressed by a variety of art-known methods. For example, genes encoding their light and heavy chain V regions may first be synthesized from overlapping oligonucleotides or by PCR mutagenesis of an earlier prepared variant of the desired gene. Because of the degeneracy of the genetic code, a variety of DNA sequences encode each antibody amino acid sequence. All DNA sequences encoding the antibodies described in this application are expressly included in the invention. However made, the genes encoding the humanized mAb light and heavy chain genes and inserted together with C regions into expression vectors (e.g., commercially available from Invitrogen) that provide the necessary regulatory regions, e.g., promoters, enhancers, poly A sites, etc. Use of the CMV promoter-enhancer is preferred. Genes for C regions are now widely available or may be readily cloned by PCR from human antibody producing cells. The light and heavy chain genes may be inserted together into a single vector or into separate vectors. The expression vectors may then be transfected using various art-known methods such as lipofection or electroporation into a variety of mammalian cell lines such as CHO or 293 or non-producing myelomas including Sp2/0 and NS0, and cells expressing the antibodies selected by appropriate antibiotic selection. See, e.g., U.S. Pat. No. 5,530,101. Larger amounts of antibody may be produced by growing the cells in commercially available bioreactors.

Once expressed, the humanized mAbs of the invention may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 90 or 95% homogeneity are preferred, and 98% or 99% or more homogeneity most preferred, for pharmaceutical uses.

3. Therapeutic Methods

In a preferred embodiment, the present invention provides a pharmaceutical formulation comprising the humanized antibodies described herein. Pharmaceutical formulations of the antibodies contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art (See Remington's Pharmaceutical Science $16^{th}$ edition, Osol, A. Ed. 1980). The mAb is typically present at a concentration of 1-100 mg/ml, e.g., 10 mg/ml.

In another preferred embodiment, the invention provides a method of treating a patient with a disease using a humanized anti-HGF mAb such as humanized L2G7, e.g., HuL2G7, in a pharmaceutical formulation. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease (e.g., a tumor), or encapsulated into carrying agents such as liposomes. The dose given is sufficient to alleviate the condition being treated ("therapeutically effective dose") and is likely to be 0.1 to 5 mg/kg body weight, for example 1, 2, 3 or 4 mg/kg, but may be as high as 10 mg/kg or even 15 or 20 mg/kg. A fixed unit dose may also be given, for example, 50, 100, 200, 500 or 1000 mg, or the dose may be based on the patient's surface area, e.g., 100 mg/$M^2$. Usually between 1 and 8 doses, (e.g., 1, 2, 3, 4, 5, 6, 7 or 8) are administered to treat cancer, but 10, 20 or more doses may be given. The mAb can be administered daily, biweekly, weekly, every other week, monthly or at some other interval, depending, e.g. on the half-life of the mAb, for 1 week, 2 weeks, 4 weeks, 8 weeks, 3-6 months or longer. Repeated courses of treatment are also possible, as is chronic administration.

Diseases especially susceptible to therapy with the humanized anti-HGF mAbs of this invention, e.g., HuL2G7, include solid tumors believed to require angiogenesis or to be associated with elevated levels of HGF, for example ovarian cancer, breast cancer, lung cancer (small cell or non-small cell), colon cancer, prostate cancer, pancreatic cancer, gastric cancer, liver cancer, head-and-neck tumors, melanoma and sarcomas of children or adults, and brain tumors. Indeed, the methods of this invention, especially systemic treatment with a humanized L2G7 mAb, are especially applicable to the treatment of brain tumors including meningiomas; gliomas including ependymomas, oligodendrogliomas, and all types of astrocytomas (low grade, anaplastic, and glioblastoma multiforme or simply glioblastoma); medullablastomas, gangliogliomas, schwannomas, chordomas; and brain tumors primarily of children including primitive neuroectodermal tumors. Both primary brain tumors (i.e., arising in the brain) and secondary or metastatic brain tumors can be treated by the methods of the invention. Other diseases suitable for treatment by the methods of the invention are those associated with undesired angiogenesis such as diabetic retinopathy, age-related macular degeneration, rheumatoid arthritis and psoriasis.

In an especially preferred embodiment, the humanized anti-HGF mAb, e.g., HuL2G7, is administered together with (i.e., before, during or after) other anti-cancer therapy. For example, the mAb may be administered together with any one or more of the chemotherapeutic drugs known to those of skill in the art of oncology, for example alkylating agents such as carmustine, chlorambucil, cisplatin, carboplatin, oxiplatin, procarbazine, and cyclophosphamide; antimetabolites such as fluorouracil, floxuridine, fludarabine, gemcitabine, methotrexate and hydroxyurea; natural products including plant alkaloids and antibiotics such as bleomycin, doxorubicin, daunorubicin, idarubicin, etoposide, mitomycin, mitoxantrone, vinblastine, vincristine, and Taxol (paclitaxel) or related compounds such as Taxotere®; agents specifically approved for brain tumors including temozolomide and Gliadel® wafer containing carmustine; and other drugs including irinotecan and Gleevec® and all approved and experimental anti-cancer agents listed in WO 2005/017107 A2 (which is herein incorporated by reference). Other agents with which the humanized anti-HGF mAb can be administered include biologics such as monoclonal antibodies, including Herceptin™ against the HER2 antigen, Avastin™ against VEGF, or antibodies to the EGF receptor, as well as small molecule anti-angiogenic or EGF receptor antagonist drugs. In addition, the humanized anti-HGF mAb can be used together with radiation therapy or surgery.

Treatment (e.g., standard chemotherapy) including the humanized anti-HGF mAb antibody, e.g., HuL2G7, can increase the median progression-free survival or overall survival time of patients with these tumors (e.g., ovarian, breast, lung, pancreas, brain and colon, especially when relapsed or refractory) by at least 30% or 40% but preferably 50%, 60% to 70% or even 100% or longer, compared to the same treatment (e.g., chemotherapy) but without anti-HGF mAb. In addition or alternatively, treatment (e.g., standard chemotherapy) including the anti-HGF mAb can increase the complete response rate, partial response rate, or objective response rate (complete +partial) of patients with these tumors (e.g., ovarian, breast, lung, pancreas, brain and colon, especially when relapsed or refractory) by at least 30% or 40% but preferably 50%, 60% to 70% or even 100% compared to the same treatment (e.g., chemotherapy) but without the anti-HGF mAb. For brain tumors such as glioblastomas, treatment with the humanized anti-HGF mAb, alone or in combination with other agents, preferably provides a partial, complete or objective response rate of at least 5% or 10%, more preferably 20% or 25% or 30%, and most preferably 40%, 50% or higher.

Typically, in a clinical trial (e.g., a phase 11, phase II/III or phase III trial), the aforementioned increases in median progression-free survival and/or response rate of the patients treated with standard therapy plus the humanized anti-HGF mAb, e.g., HuL2G7, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

4. Other Methods

The humanized anti-HGF mAbs of the invention also find use in diagnostic, prognostic and laboratory methods. They may be used to measure the level of HGF in a tumor or in the circulation of a patient with a tumor, and therefore to follow and guide treatment of the tumor. For example, a tumor associated with high levels of HGF would be especially susceptible to treatment with a humanized anti-HGF mAb. In particular embodiments, the mAbs can be used in an ELISA or radioimmunoassay to measure the level of HGF, e.g., in a tumor biopsy specimen or in serum or in media supernatant of HGF-secreting cells in cell culture. For various assays, the anti-HGF mAb may be labeled with fluorescent molecules, spin-labeled molecules, enzymes or radioisotopes, and may be provided in the form of kit with all the necessary reagents to perform the assay for HGF. In other uses, the anti-HGF mAbs are used to purify HGF, e.g., by affinity chromatography.

EXAMPLES

1. Construction of a Humanized L2G7 Antibody

The generation of the mouse anti-HGF mAb L2G7, which neutralizes all tested biological activities of HGF, has already been described (Kim et al., US20050019327 filed Aug. 13, 2004, and Kim et al. Clin Cancer Res 12:1292, 2006). The first step to humanize L2G7 was to clone its light and heavy chain genes, which was accomplished essentially according to the method of Co et al., J. Immunol. 148:1149, 1992. Briefly, RNA was prepared from $10^6$ L2G7 (IgG2a, K) hybridoma cells using an RNeasy Mini Kit (Qiagen) followed by first strand cDNA synthesis with random primers using a kit from Stratagene and addition of dG tails with terminal deoxynucleotidyl transferase (Promega). The heavy and light chain V regions were respectively amplified from the cDNA with a primer annealing to the dG tails and a primer annealing to the N-terminal region of Cy2a for the heavy chain and a primer annealing to the N-terminal region of $C_K$ for the light chain, using a high fidelity polymerase AccuPrime Pfx (Invitrogen). Bands of appropriate sizes were gel purified from the PCR reactions, and sequenced directly or cloned and then sequenced, using the dideoxy termination method with an automated sequencer. A single cDNA sequence was found for the heavy chain, which is shown after translation in FIG. 1A. Two different apparently non-aberrant light chain cDNA sequences were found, but amino acid sequencing of the N-terminus of isolated L2G7 light chain revealed only one of these chains, the translated amino acid sequence of which is shown in FIG. 1B.

To express a chimeric form of L2G7 and later the humanized mAb, expression vectors similar to the pVk and pVg1 vectors described in Co et al., J. Immunol. 148:1149, 1992, which contain the human $C_K$ and $C_{y1}$ genes, were constructed from commercially available vectors and DNA fragments. However, the light chain vector has the hyg selectable marker instead of gpt, and the heavy chain vector has the neo selectable marker instead of Dhfr. The cloned $V_L$ and $V_H$ genes were subcloned into the appropriate sites of these vectors to generate expression plasmids for the chimeric L2G7 (chL2G7) mAb light and heavy chain genes. The chL2G7 mAb was produced and shown to bind HGF as well as L2G7 does, proving that correct light and heavy chain V regions had been cloned.

To design a humanized L2G7 mAb, the methods of Queen et al., U.S. Pat. Nos. 5,530,101 and 5,585,089 were generally followed. The National Center for Biotechnology Information (NCBI) database of human antibody sequences was scanned, and the human $V_H$ sequence AAC18323 and $V_K$ sequence BAC 01726 were respectively chosen to serve as acceptor sequences for the L2G7 $V_H$ and $V_L$ sequences because they have particularly high framework homology (i.e., sequence identity) to them. A computer program, Deep View Swiss-Pdb Viewer, available on the worldwide web (expasy.org/spdbv/), was used to construct a molecular model of the L2G7 variable domain, which was used to locate the amino acids in the L2G7 framework that are close enough to the CDRs to potentially interact with them. To design the humanized L2G7 heavy and light chain variable regions, the CDRs from the mouse L2G7 mAb were first conceptually grafted into the acceptor framework regions. At framework positions where the computer model suggested significant contact with the CDRs, which may be needed to maintain the CDR conformation, the amino acids from the mouse antibody were substituted for the original human framework amino acids. For the humanized L2G7 mAb designated HuL2G7, this was done at residues 29, 30 (within Chothia hypervariable loop H1), 48, 66, 67, 71 and 94 of the heavy chain and at residues 3 and 60 of the light chain, using Kabat numbering. In addition, amino acid 1 of the heavy chain was replaced with B (Glu) because this amino acid is less likely than Q (Gln) to undergo derivatization in the antibody protein. The heavy and light chain V region sequences of HuL2G7 are shown aligned against the respective L2G7 and acceptor V regions in FIGS. 2A and 2B, with the CDRs and substituted amino acids highlighted.

The invention also provides variant humanized L2G7 mAbs whose mature heavy and light chain variable regions differ from the sequences of HuL2G7 by a small number (e.g., typically no more than 1, 2, 3, 5 or 10) of replacements, deletions or insertions, usually in the framework but possibly in the CDRs. In particular, only a subset of the substitutions described above can be made in the acceptor frameworks, or additional substitution(s) can be made, e.g., the mouse L2G7 $V_H$ amino acid 69F may replace the acceptor amino acid 69M. On the other hand, the $V_H$ amino acid 1 E may instead be Q. Indeed, many of the framework residues not in contact with the CDRs in HuL2G7 can accommodate substitutions of amino acids from the corresponding positions of L2G7 or other mouse or human antibodies, and even many potential CDR-contact residues are also amenable to substitution or even amino acids within the CDRs.

Most often the replacements made in the variant humanized L2G7 sequences are conservative with respect to the replaced HuL2G7 amino acids. Preferably, replacements in HuL2G7 (whether or not conservative) have no substantial effect on the binding affinity or potency of the humanized mAb, that is, its ability to neutralize the biological activities of HGF (e.g., the potency in some or all of the assays described herein of the variant humanized L2G7 mAb is essentially the same, i.e., within experimental error, as that of HuL2G7). Preferably the mature variant light and heavy chain V region sequences are at least 90%, more preferably at least 95%, and most preferably at least 98% identical to the respective HuL2G7 mature light and heavy chain V regions. Alternatively, other human antibody variable regions with high sequence identity to those of L2G7 are also suitable to provide the humanized antibody framework, especially kappa V regions from human subgroup I and heavy chain V regions from human subgroup I, or consensus sequences of these subgroups.

The exemplary mAb HuL2G7 discussed in the Examples below has human K and γ1 constant regions and is therefore an IgG1: the complete sequences of the HuL2G7 heavy and light chain genes including signal peptides are shown in FIG. 3A and FIG. 3B. (Of course, the signal peptides are cleaved off and are not part of HuL2G7.) However, it is understood that IgG1 mAbs of other (IgG1, K) allotypes are encompassed by the designation HuL2G7. Humanized mAbs of other isotypes (e.g., IgG2, IgG3 and IgG4) can be made by combining the HuL2G7 variable regions with the appropriate human constant regions. Replacements can be made in the HuL2G7 constant regions to reduce or increase effector function such as complement-mediated cytotoxicity or ADCC (see, e.g., Winter et al., U.S. Pat. No. 5,624,821; Tso et al., .U.S Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Specifically but without limitation, HuL2G7 having mutations in the IgG constant region to a Gln at position 250 and/or a Leu at position 428 are embodiments of the present invention.

Having designed the HuL2G7 mAb, i.e., having chosen the amino acid sequences of its light and heavy chain V regions (FIG. 2 and FIG. 3), DNA sequences encoding the V regions (including signal peptides) were routinely chosen via the genetic code; the sequences began with CTCGAGACCACC (SEQ ID NO: 1) before the initiating ATG codon to provide a restriction site for cloning and a Kozak translation initiation signal. These genes were synthesized commercially by Genscript Corp. (Piscataway, N.J.). Alternatively, the method of Co et at., J. Immunol. 148:1149, 1992 can be used to synthesize each V region gene. Briefly, two pairs of overlapping oligonucleotides on alternating strands are synthesized (Applied Biosystems DNA synthesizer), which together encompass the entire gene. The oligonucleotides are 110 to 140 bases long with 15-base overlaps. Double-stranded DNA fragments are synthesized using Klenow polymerase from the 5' pair of oligos and separately from the 3' pair. The 5' DNA fragment is cleaved with the restriction enzymes cutting at the 5' end and at the center of the V region gene. The 3' DNA fragment is cleaved with the restriction enzymes cutting at the center and at the 3' end of the V region gene. Each cleaved fragment is inserted into a suitable cloning vector and transformed into *E. coli*, and DNA from a number of isolates is sequenced to find fragments that have completely correct sequences. For each gene, a 3-way ligation is then performed to insert the correct 5' and 3' fragments into the appropriate expression vector to form the complete gene, the sequence of which is verified.

To produce the HuL2G7 mAb, human renal epithelial 293-F cells (Invitrogen) were cultured in FreeStyle 293 expression medium (FS medium; Invitrogen) and resuspended in FS medium at $10^6$ cells /2 ml /macrowell. The HuL2G7 light and heavy chain expression vector DNAs (1 μg of each) were incubated with 3 μl of Fugene 6 (Roche) in 100 μl FS medium for 30 min at RT; the mixture was then added to the cells. After 48 hr incubation, transfected cells were cultured in the presence of 1 mg/ml G418 to select for cells expressing neo and then spread into 96-well tissue culture plates (100 μl/well). After approximately 2 weeks, when wells containing viable cells had become confluent, culture supernatants from those wells were tested for the presence and quantity of HuL2G7 by ELISA. Transfected cells may secrete an imbalance of light and heavy chains, so to ensure that only complete HuL2G7 is measured, this ELISA uses goat anti-human Fc as a capture agent and biotinylated anti-human kappa as a detection reagent. The chL2G7 mAb was expressed similarly. Clones of cells expressing relatively high levels of ChL2G7 and HuL2G7 were respectively expanded and grown in FS medium. Antibody was purified from culture supernatants using protein A affinity chromatography and analyzed for purity by SDS-PAGE.

2. Properties of HuL2G7

To compare the binding affinity of HuL2G7 with that of ChL2G7 and L2G7, a competitive binding experiment was performed. A microtiter plate was coated with 50 μl/well of 2 μg/ml of goat anti-human IgG-Fc (GαhIgG-Fc) in PBS overnight at 4° C. and blocked with 2% BSA for 1 hr at RT. After washing, the plate was incubated with 50 μl/well ChL2G7 mAb (2 μg/well) for 1 hr at RT, followed after washing by 50 μl/well of human IgG (10 μg/ml) for 1 hr to reduce background. After washing, wells of the plate were separately incubated for 1 hr with 50 μl/well of various concentrations of purified HuL2G7, ChL2G7 or L2G7 as competitor together with 50 µl/well of HGF-Flag (1 µg/ml). After washing, the plates were then incubated with 50 µl/well of HRP-M2 anti-Flag mAb (Invitrogen) and the bound HRP-anti-Flag M2 detected by the addition of tetramethylbenzidine substrate. FIG. 4 shows that HuL2G7, ChL2G7 and L2G7 competed essentially equally well with the L2G7 bound to the plate for binding to the soluble HGF-Flag, indicating that these three mAbs have very similar affinity.

Figure 5:
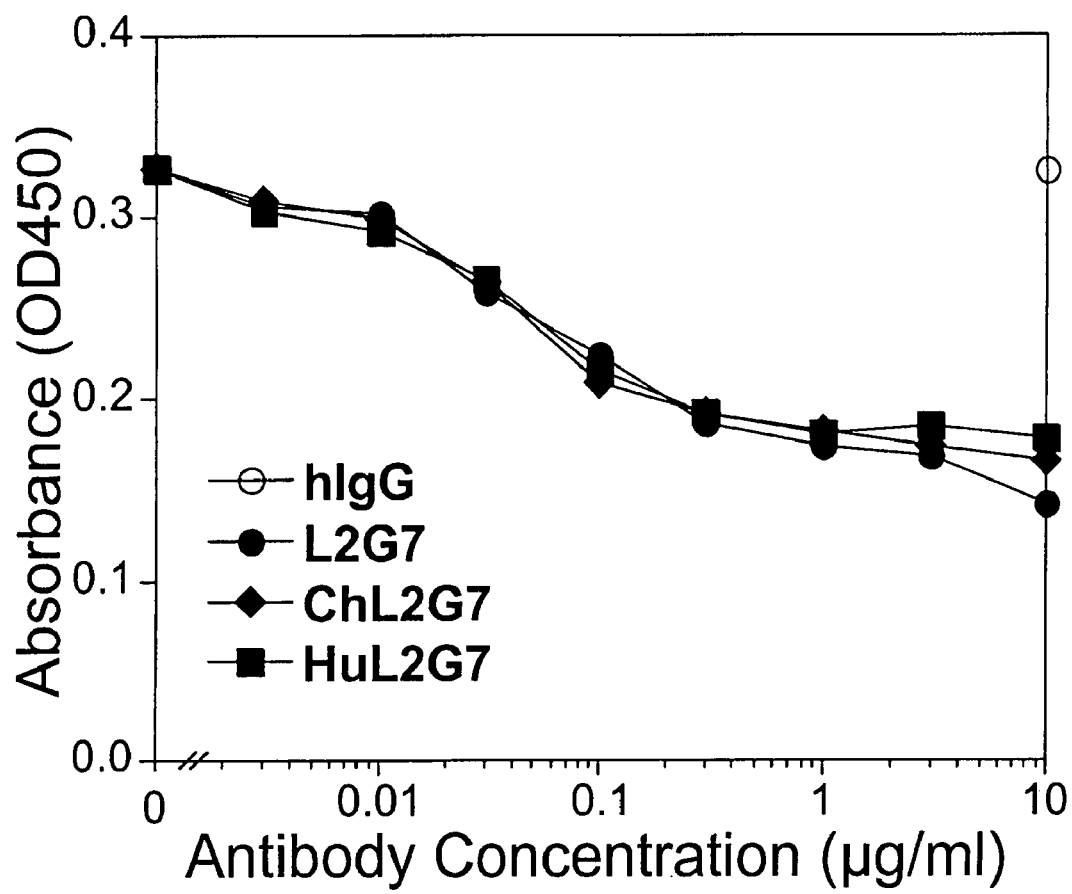
FIG. 5. Relative ability of HuL2G7, ChL2G7 and L2G7 to block binding of HGF to Met.

A key biological activity of HGF is the ability to bind to its receptor cMet, so the ability of the HuL2G7, ChL2G7 and L2G7 mAbs to inhibit binding of HGF to Met was compared. Met was used in the form of Met-Fc and HGF in the form of HGF-Flag, which were prepared as described (Patent application U.S. Ser. No. 10/917,915 filed August 13, 2004, and Kim et al. Clin Cancer Res 12:1292, 2006). A microtiter plate was coated with 50 µl/well of 2 µg/mi each of two anti-Met mAbs (Galaxy Biotech) in PBS overnight at 4° C. (alternatively 2 µg/ml GαhIgG-Fc may be used) and blocked with 2% BSA for 1 hr at RT. After washing the plates, 50 µl/well of Met-Fc (1 µg/ml) was added to each well for 1 hr at RT, followed after washing by 50 µl well of human IgG (10 µg/ml) for 1 hr to reduce background After washing the plates, 50 µl/well of HGF-Flag (0.5 µg/ml) preincubated with various concentrations of mAbs was added to each well for 1 hr. After washing, the plates were incubated with 50 µl/well of HRP-M2 anti-Flag mAb (Invitrogen), and the bound HRP-anti-Flag M2 detected by the addition of the substrate as described above. FIG. 5 shows that HuL2G7, ChL2G7 and L2G7 blocked binding of HGF to Met equally well, so these mAbs have very similar activity in this assay.

Figure 6:
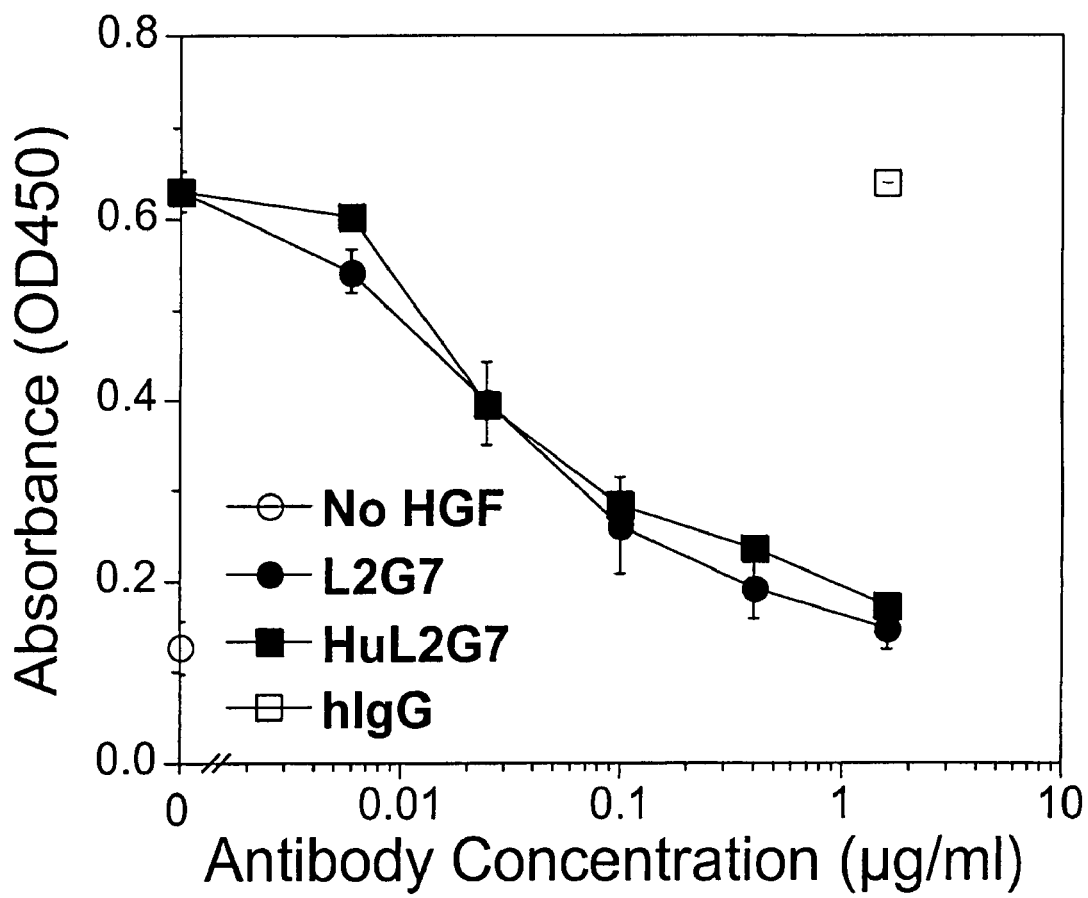
FIG. 6. Relative ability of HuL2G7 and L2G7 to inhibit HGF-induced proliferation of Mv 1 Lu cells.

Another important biological activity of HGF is the ability to stimulate proliferation of certain cells, including Mv 1 Lu mink lung epithelial cells. To compare the ability of HuL2G7 and L2G7 to neutralize this activity of HGF, Mv 1 Lu cells ($2 \times 10^4$ cells/100 µL/well) grown in DMEM containing 10% FCS were resuspended in serum-free DMEM and stimulated with 100 µL/well of HGF (40 ng/mL) plus transforming growth factor-β1 (1 ng/mL, R&D Systems) to reduce background and various concentrations of HuL2G7, L2G7 or irrelevant control human antibody. The level of cell proliferation was determined by the addition of WST-1 (Roche Applied Science) for 14 hours. FIG. 6 shows that the HuL2G7 and L2G7 had equal inhibitory activity in this assay. In summary, HuL2G7 was at least equally as active as L2G7 in all assays used, and is therefore fully neutralizing: no activity of L2G7 was lost in the humanization process.

3. Ability of HuL2G7 to Inhibit Tumor Growth in vivo

Figure 7:
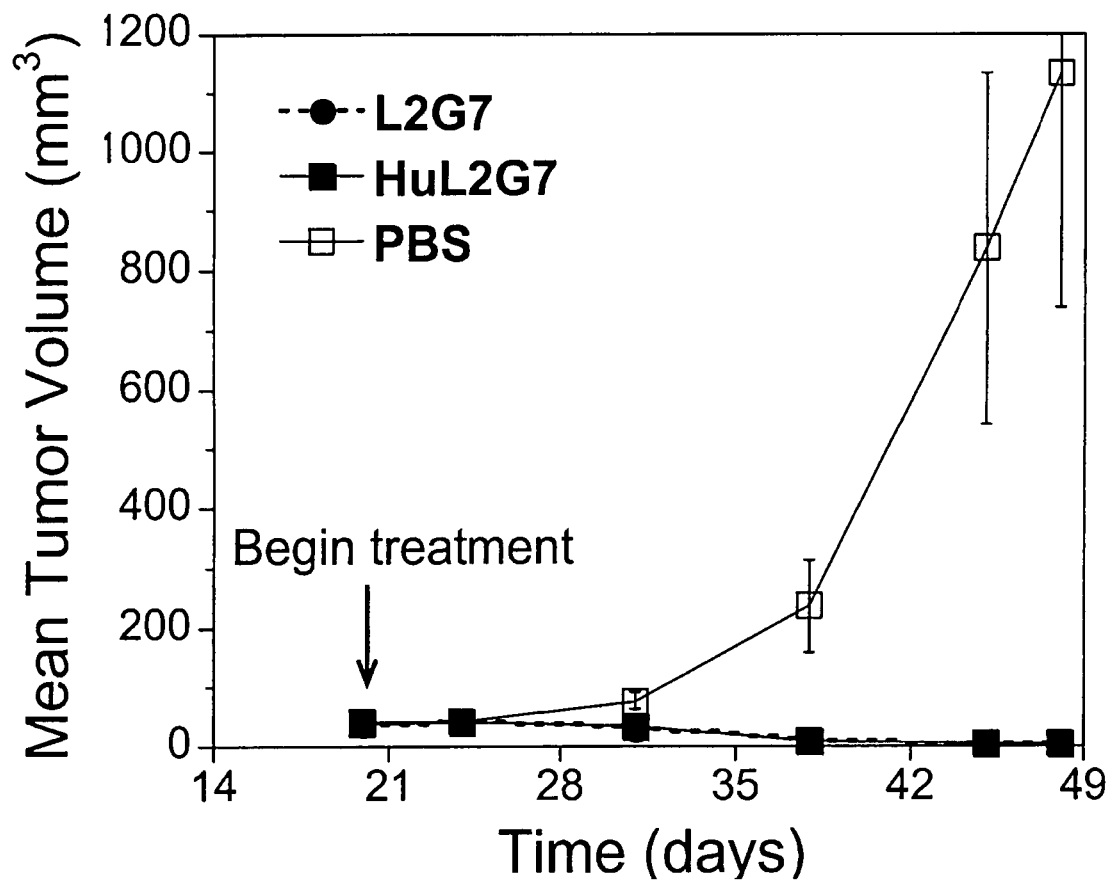
FIG. 7. Effect of treatment with HuL2G7 or L2G7 mAb or PBS control on growth of U87 subcutaneous xenografts in groups of NIH III Beige/Nude mice. Arrow indicates when injections began, and error bars show standard error of the mean (s.e.m). The symbols for L2G7 and HuL2G7 superimpose and cannot be distinguished in the figure.
Figure 8:
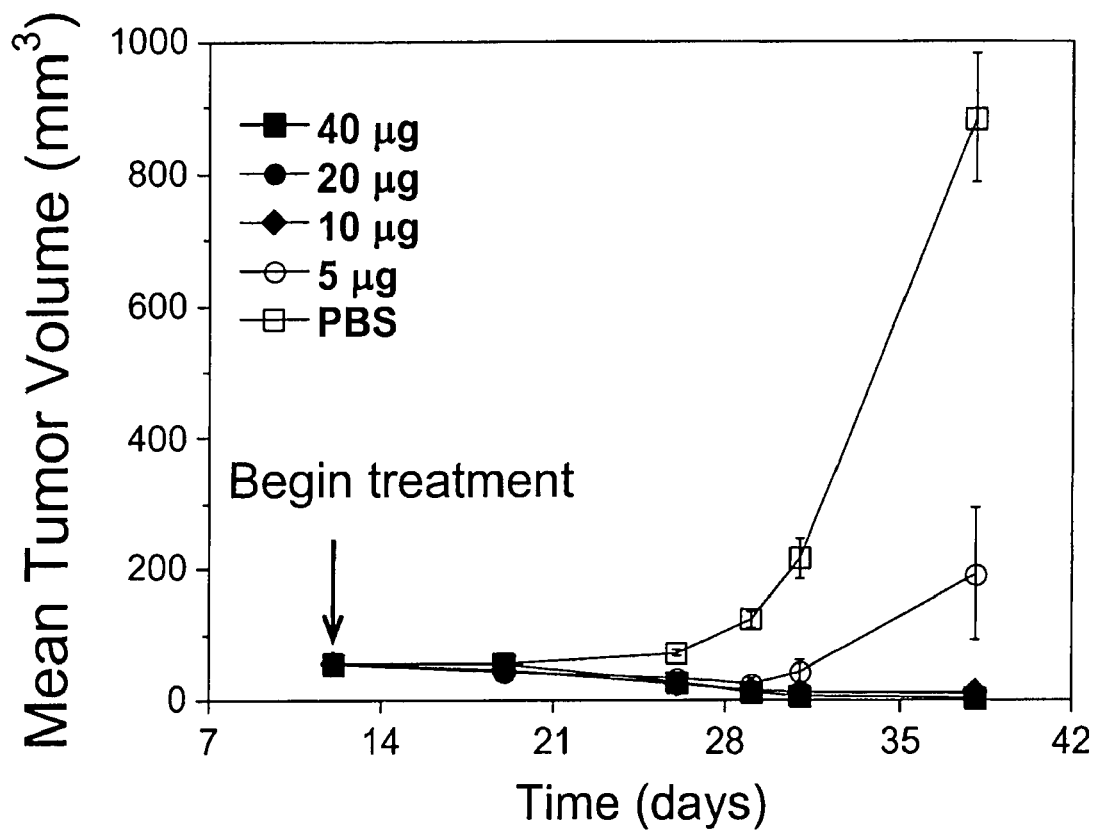
FIG. 8. Effect of four different dose levels of HuL2G7 on growth of U87 subcutaneous xenografts in groups of NIH III Beige/Nude mice. Arrow indicates when injections began, and error bars show s.e.m.

It has already been shown that L2G7 mAb is able to completely inhibit the growth of U87 glioma xenografts in nude mouse models (Patent application U.S. Ser. No. 10/917,915 filed Aug. 13, 2004, and Kim et al. Clin Cancer Res 12:1292, 2006). To verify that HuL2G7 also has this ability, the same experimental procedure was used. Briefly, female 4-6 week-old NIH III Xid/Beige/Nude mice (Charles River Laboratories) were injected s.c. with $10^7$ cells in 0.1 ml of PBS in the dorsal areas. When the tumor size reached ~50 mm$^3$, the mice were randomly divided into groups (n=6 per group) and injected with 40 ug HuL2G7, L2G7 or control PBS i.p. twice weekly in a volume of 0.1 ml PBS. Tumor volumes were determined weekly by measuring two dimensions (length, a, and width, b) and calculating volume as $V=ab^2/2$. FIG. 7 shows that HuL2G7 and L2G7 inhibited tumor growth indistinguishably in this assay. To further define the ability of HuL2G7 to inhibit growth of tumor xenografts, four different doses of the mAb, 40 µg, 20 µg, 10 µg and 5 µg, were used in a similar experiment. FIG. 8 shows that even the remarkably low dose of 10 µg twice weekly was able to completely inhibit tumor growth, while the even lower dose of 5 µg gave good but incomplete inhibition. Similarly, when administered systemically HuL2G7 effectively inhibits growth of intracranial U87 xenographs.

Although the invention has been described with reference to the presently preferred embodiments, it should be understood that various modifications can be made without departing from the invention.

All publications, patents and patent applications cited are herein incorporated by reference in their entirety for all purposes to the same extent as if each individual publication, patent and patent application was specifically and individually indicated to be incorporated by reference in its entirety for all purposes.

The L2G7 hybridoma has been deposited on Apr. 29, 2003 with the American Type Culture Collection, P.O. Box 1549 Manassas, Va. 20108, as ATCC Number PTA-5162 under the Budapest Treaty. This deposit will be maintained at an authorized depository and replaced in the event of mutation, non-viability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

We claim:

1. A humanized monoclonal antibody (mAb) that binds and neutralizes human Hepatocyte Growth Factor comprising a mature heavy chain variable region having the amino acid sequence of SEQ ID NO:5 and a mature light chain variable region having the amino acid sequence of SEQ ID NO:8.

2. A humanized monoclonal antibody (mAb) that binds and neutralizes human Hepatocyte Growth Factor comprising a mature heavy chain variable region having the amino acid sequence of SEQ ID NO:5 except the first amino acid is replaced with Gln and a mature light chain variable region having the amino acid sequence of SEQ ID NO:8.

3. A humanized monoclonal antibody (mAb) that binds and neutralizes human Hepatocyte Growth Factor (HGF), the humanized antibody comprising humanized heavy and light chains, the humanized heavy chain comprising CDRs from L2G7 (ATCC PTA-5162) and a human heavy chain variable region framework provided that at least positions H29, H30, H48, H66, H67, H71, H94 are occupied by the amino acids occupying the corresponding position in the L2G7 heavy chain; the humanized light chain comprising CDRs from L2G7 and a human light chain variable region framework provided that at least positions L3 and L60 are occupied by the amino acid occupying the corresponding position in the L2G7 light chain.

4. A humanized mAb of claim 1, 2 or 3 which is of IgG1, K isotype.

5. A humanized mAb of claim 3 which neutralizes biological activities of HGF as well as L2G7 (ATCC PTA-5162) does.

6. The humanized monoclonal antibody (mAb) of claim 3, further provided position H1 is occupied by Glu.

7. A cell line producing a mAb of claim 1, 2 or 3.

8. A pharmaceutical composition comprising a mAb of claim 1, 2 or 3.

* * * * *

SEQUENCE LISTING

```
<160> NUMBER OF SEQ ID NOS: 11

<210> SEQ ID NO 1
<211> LENGTH: 12
<212> TYPE: DNA
<213> ORGANISM: Artificial
<220> FEATURE:
<223> OTHER INFORMATION: Cloning restriction site
```

-continued

```
<400> SEQUENCE: 1
ctcgagacca cc                                                          12

<210> SEQ ID NO 2
<211> LENGTH: 120
<212> TYPE: PRT
<213> ORGANISM: Artificial
<220> FEATURE:
<223> OTHER INFORMATION: L2G7 mature heavy chain

<400> SEQUENCE: 2

Gln Val Gln Leu Gln Gln Ser Gly Ala Asp Leu Met Lys Pro Gly Ala
 1               5                  10                  15

Ser Val Lys Ile Ser Cys Lys Ala Thr Gly Tyr Thr Phe Ser Gly Asn
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asn Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly His Tyr Tyr Gly Ser Ser Trp Asp Tyr Trp Gly Gln
            100                 105                 110

Gly Thr Thr Leu Thr Val Ser Ser
        115                 120

<210> SEQ ID NO 3
<211> LENGTH: 108
<212> TYPE: PRT
<213> ORGANISM: Artificial
<220> FEATURE:
<223> OTHER INFORMATION: L2G7 mature light chain

<400> SEQUENCE: 3

Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105

<210> SEQ ID NO 4
<211> LENGTH: 120
<212> TYPE: PRT
<213> ORGANISM: Artificial
<220> FEATURE:
<223> OTHER INFORMATION: L2G7 heavy chain mature variable region

<400> SEQUENCE: 4
```

-continued

```
Gln Val Gln Leu Gln Gln Ser Gly Ala Asp Leu Met Lys Pro Gly Ala
1               5                   10                  15

Ser Val Lys Ile Ser Cys Lys Ala Thr Gly Tyr Thr Phe Ser Gly Asn
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asn Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
            85                  90                  95

Ala Arg Gly Gly His Tyr Tyr Gly Ser Ser Trp Asp Tyr Trp Gly Gln
                100                 105                 110

Gly Thr Thr Leu Thr Val Ser Ser
            115                 120
```

<210> SEQ ID NO 5
<211> LENGTH: 120
<212> TYPE: PRT
<213> ORGANISM: Artificial
<220> FEATURE:
<223> OTHER INFORMATION: HuL2G7 heavy chain mature variable region

<400> SEQUENCE: 5

```
Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Ser Gly Asn
            20                  25                  30

Trp Ile Glu Trp Val Arg Gln Ala Pro Gly Lys Gly Leu Glu Trp Ile
        35                  40                  45

Gly Glu Ile Leu Pro Gly Ser Gly Asn Thr Asn Tyr Asn Glu Lys Phe
    50                  55                  60

Lys Gly Lys Ala Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly His Tyr Tyr Gly Ser Ser Trp Asp Tyr Trp Gly Gln
                100                 105                 110

Gly Thr Leu Val Thr Val Ser Ser
            115                 120
```

<210> SEQ ID NO 6
<211> LENGTH: 125
<212> TYPE: PRT
<213> ORGANISM: Artificial
<220> FEATURE:
<223> OTHER INFORMATION: AAC18323 heavy chain mature variable region

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60
```

```
Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Val Gly Arg Cys Ser Ser Thr Ser Cys Tyr His Pro Leu
            100                 105                 110

Asp Tyr Trp Gly Gln Gly Thr Leu Val Thr Val Ser Ser
        115                 120                 125

<210> SEQ ID NO 7
<211> LENGTH: 108
<212> TYPE: PRT
<213> ORGANISM: Artificial
<220> FEATURE:
<223> OTHER INFORMATION: L2G7 light chain mature variable region

<400> SEQUENCE: 7

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105

<210> SEQ ID NO 8
<211> LENGTH: 108
<212> TYPE: PRT
<213> ORGANISM: Artificial
<220> FEATURE:
<223> OTHER INFORMATION: HuL2G7 light chain mature variable region

<400> SEQUENCE: 8

Asp Ile Val Met Thr Gln Ser Pro Ser Ser Leu Ser Ala Ser Val Gly
1               5                   10                  15

Asp Arg Val Thr Ile Thr Cys Lys Ala Ser Glu Asn Val Val Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Gly Tyr Ser Tyr Pro Tyr
                85                  90                  95

Thr Phe Gly Gln Gly Thr Lys Leu Glu Ile Lys Arg
            100                 105

<210> SEQ ID NO 9
<211> LENGTH: 108
<212> TYPE: PRT
```

```
<213> ORGANISM: Artificial
<220> FEATURE:
<223> OTHER INFORMATION: BAC01726 lighr chain mature variable region

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg
            100                 105

<210> SEQ ID NO 10
<211> LENGTH: 469
<212> TYPE: PRT
<213> ORGANISM: Artificial
<220> FEATURE:
<223> OTHER INFORMATION: HuL2G7 heavy chain

<400> SEQUENCE: 10

Met Asp Cys Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys
            20                  25                  30

Pro Gly Ala Ser Val Lys Val Ser Cys Lys Val Ser Gly Tyr Thr Phe
        35                  40                  45

Ser Gly Asn Trp Ile Glu Trp Val Arg Gln Ala Pro Gly Lys Gly Leu
50                  55                  60

Glu Trp Ile Gly Glu Ile Leu Pro Gly Ser Gly Asn Thr Asn Tyr Asn
65                  70                  75                  80

Glu Lys Phe Lys Gly Lys Ala Thr Met Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly His Tyr Tyr Gly Ser Ser Trp Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220
```

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 11
<211> LENGTH: 234
<212> TYPE: PRT
<213> ORGANISM: Artificial
<220> FEATURE:
<223> OTHER INFORMATION: HuL2G7 light chain

<400> SEQUENCE: 11

Met Glu Ala Pro Ala Gln Leu Leu Phe Leu Leu Leu Leu Trp Leu Pro
1               5                   10                  15

Asp Thr His Gly Asp Ile Val Met Thr Gln Ser Pro Ser Ser Leu Ser
                20                  25                  30

Ala Ser Val Gly Asp Arg Val Thr Ile Thr Cys Lys Ala Ser Glu Asn
            35                  40                  45

Val Val Thr Tyr Val Ser Trp Tyr Gln Gln Lys Pro Gly Lys Ala Pro
        50                  55                  60

Lys Leu Leu Ile Tyr Gly Ala Ser Asn Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gly Gln Gly Tyr
            100                 105                 110

```
-continued

Ser Tyr Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```